(12) United States Patent
Seedhom et al.

(10) Patent No.: US 11,357,487 B2
(45) Date of Patent: Jun. 14, 2022

(54) MEDICAL PROBE, ASSEMBLY AND METHOD

(71) Applicant: Xiros Limited, Leeds (GB)

(72) Inventors: Bahaa Botros Seedhom, Leeds (GB); Martin James Bennett Stanley, Leeds (GB)

(73) Assignee: Xiros Limited, Leeds (GB)

( * ) Notice: Subject to any disclaimer, the term of this patent is extended or adjusted under 35 U.S.C. 154(b) by 169 days.

(21) Appl. No.: 16/470,177

(22) PCT Filed: Dec. 15, 2017

(86) PCT No.: PCT/GB2017/053766
§ 371 (c)(1),
(2) Date: Jun. 14, 2019

(87) PCT Pub. No.: WO2018/109494
PCT Pub. Date: Jun. 21, 2018

(65) Prior Publication Data
US 2020/0022689 A1     Jan. 23, 2020

(30) Foreign Application Priority Data

Dec. 16, 2016 (GB) .................................. 1621422
Jul. 25, 2017 (GB) .................................. 1711973

(51) Int. Cl.
*A61B 17/00* (2006.01)
*A61M 25/00* (2006.01)
(Continued)

(52) U.S. Cl.
CPC ..... *A61B 17/0057* (2013.01); *A61M 25/0012* (2013.01); *A61M 27/002* (2013.01);
(Continued)

(58) Field of Classification Search
CPC ...... A61B 17/0057; A61B 2017/00623; A61B 2017/00641; A61B 2017/00654;
(Continued)

(56) References Cited

U.S. PATENT DOCUMENTS 3,757,768 A * 9/1973 Kline .............. A61M 25/09041
600/434
3,841,308 A * 10/1974 Tate .................. A61M 25/0075
600/585
(Continued)

FOREIGN PATENT DOCUMENTS

AU     2013257459 B2    12/2013
CN     202553908 U     11/2012
(Continued)

OTHER PUBLICATIONS

International Search Report and Written Opinion of the International Searching Authority, dated Feb. 27, 2018, for corresponding International Application No. PCT/GB2017/053766, 19 pages.
(Continued)

*Primary Examiner* — Julian W Woo
(74) *Attorney, Agent, or Firm* — Klarquist Sparkman, LLP

(57) ABSTRACT

A medical probe for traversing a tract in the body of a human or animal. One medical probe includes an elongate elastically deformable member including a helically wound element, and a sheath having an inner surface which contacts an outer surface of the elastically deformable member. The probe is elastically deformable, for traversing the tract, by virtue of the elastically deformable member. The probe may include a treatment element, which can be used to perform a procedure in the body of a patient. An assembly includes a probe and a treatment element. The medical probe has a particular use in the treatment of a fistula, in which the probe
(Continued)

takes the form of a fistula probe adapted to traverse a fistula tract.

29 Claims, 12 Drawing Sheets

(51) Int. Cl.
*A61M 27/00* (2006.01)
*A61B 17/04* (2006.01)
*A61B 17/06* (2006.01)
*A61B 17/32* (2006.01)

(52) U.S. Cl.
CPC .............. *A61B 2017/00623* (2013.01); *A61B 2017/00641* (2013.01); *A61B 2017/00654* (2013.01); *A61B 2017/00663* (2013.01); *A61B 2017/0498* (2013.01); *A61B 2017/06171* (2013.01); *A61B 2017/320012* (2013.01)

(58) Field of Classification Search
CPC .. A61B 2017/00663; A61B 2017/0498; A61B 2017/06171; A61B 2017/320012; A61B 2017/06085; A61B 2017/06028; A61B 2017/06095; A61M 25/0012; A61M 27/002

See application file for complete search history.

(56) References Cited

U.S. PATENT DOCUMENTS

| | | | |
|---|---|---|---|
| 9,907,885 B2 * | 3/2018 | Keighley | A61L 31/06 |
| 10,143,457 B2 * | 12/2018 | Agnew | A61B 17/12159 |
| 10,842,475 B2 * | 11/2020 | Horeman | A61B 17/0487 |
| 2007/0149951 A1 | 6/2007 | Wu et al. | |
| 2008/0051831 A1 | 2/2008 | Deal | |
| 2008/0245374 A1 | 10/2008 | Agnew | |
| 2009/0054927 A1 | 2/2009 | Agnew | |
| 2009/0275965 A1 | 11/2009 | Sibbons et al. | |
| 2011/0046607 A1 | 2/2011 | Halevy | |
| 2011/0282368 A1 * | 11/2011 | Swayze | A61B 17/0057 606/159 |
| 2013/0158594 A1 | 6/2013 | Carrison et al. | |
| 2014/0227337 A1 | 8/2014 | Keighley | |
| 2014/0277116 A1 | 9/2014 | Stanley et al. | |
| 2015/0250460 A1 | 9/2015 | Horeman et al. | |
| 2016/0000416 A1 | 1/2016 | Carrison et al. | |
| 2016/0038128 A1 | 2/2016 | Carrison | |
| 2016/0143656 A1 | 5/2016 | Tasci | |
| 2016/0157840 A1 | 6/2016 | Carrison et al. | |

FOREIGN PATENT DOCUMENTS

| | | |
|---|---|---|
| CN | 103211629 A | 7/2013 |
| CN | 203107098 U | 8/2013 |
| CN | 204106070 U | 1/2015 |
| CN | 104622428 A | 5/2015 |
| CN | 104622519 A | 5/2015 |
| CN | 204484191 U | 7/2015 |
| CN | 204563044 U | 8/2015 |
| CN | 105056311 A | 11/2015 |
| CN | 205126318 U | 4/2016 |
| EP | 0410602 A1 | 1/1991 |
| EP | 2862589 A1 | 4/2015 |
| EP | 2989995 A1 | 3/2016 |
| WO | WO1998/056448 A1 | 12/1998 |
| WO | WO2005/020823 A1 | 3/2005 |
| WO | WO2011/151659 A2 | 12/2011 |
| WO | WO2012/174468 A1 | 12/2012 |
| WO | WO2013/050404 A1 | 4/2013 |
| WO | WO2014/023962 A2 | 2/2014 |
| WO | WO2014/032813 A1 | 3/2014 |
| WO | WO2014/113461 A2 | 7/2014 |
| WO | WO2016/025404 A1 | 2/2016 |
| WO | WO2016/094727 A2 | 6/2016 |

OTHER PUBLICATIONS

International Preliminary Report on Patentability of the International Searching Authority, dated Mar. 21, 2019, for corresponding International Application No. PCT/GB2017/053766, 18 pages.

* cited by examiner

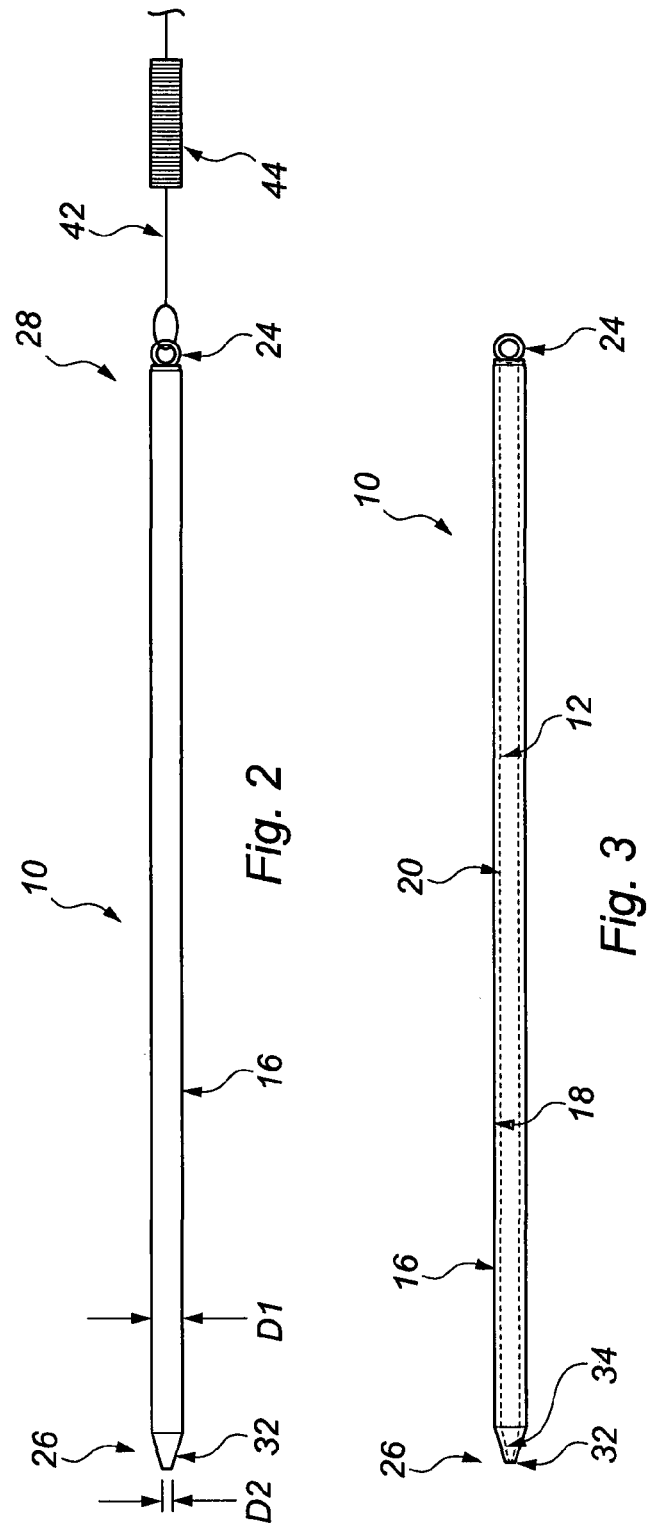

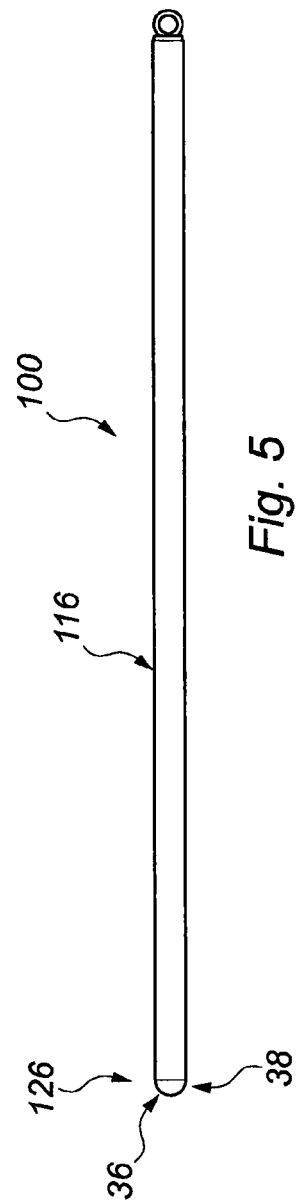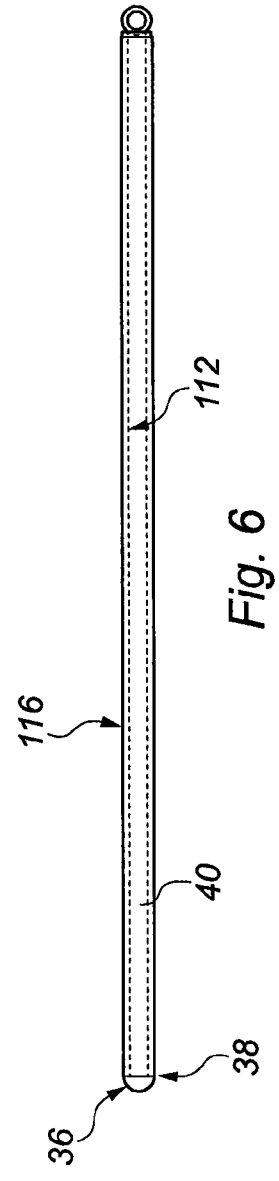

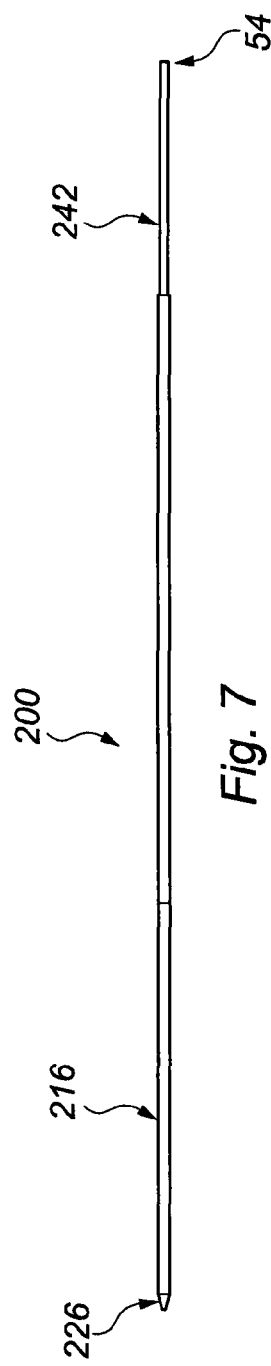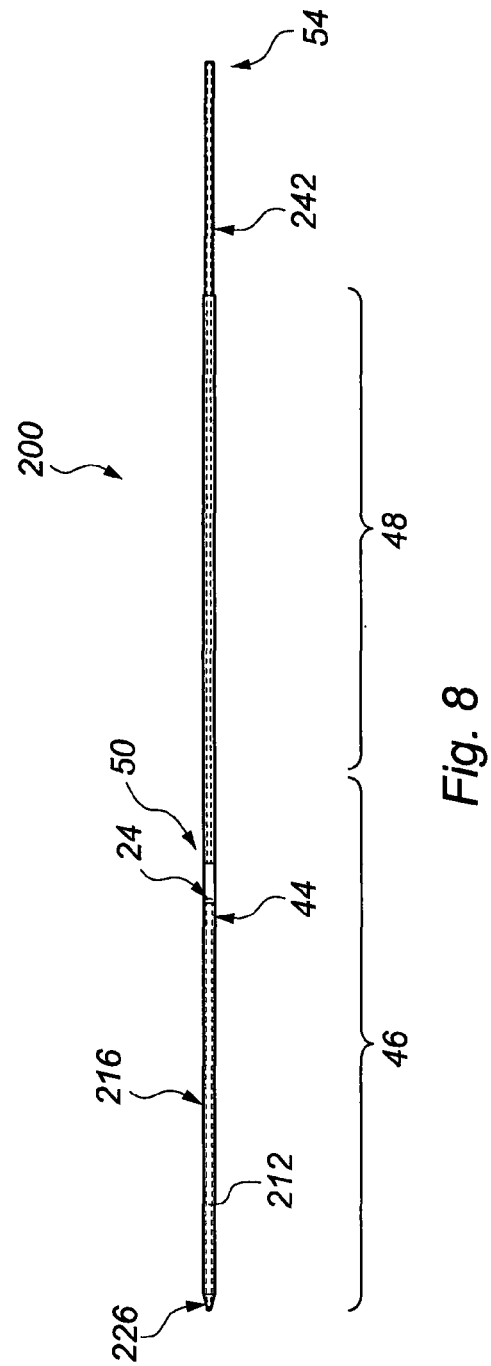

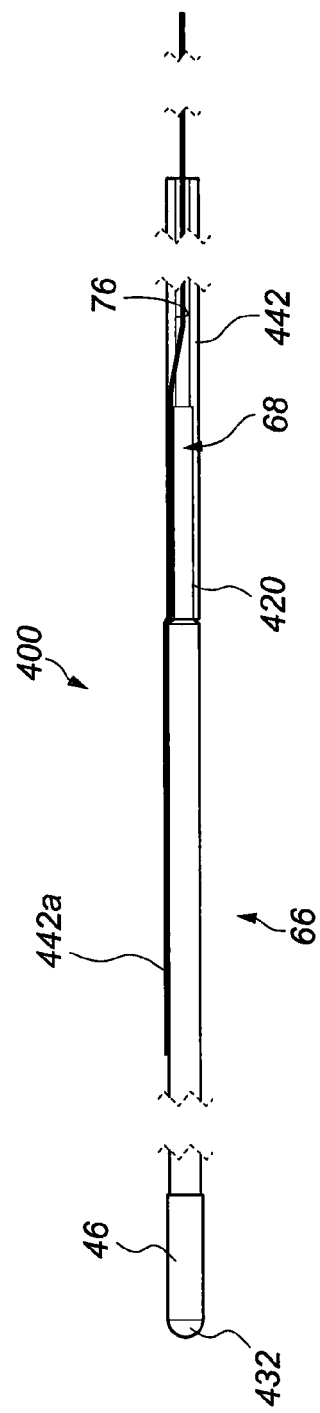

MEDICAL PROBE, ASSEMBLY AND METHOD

CROSS REFERENCE TO RELATED APPLICATIONS

This is the U.S. National Stage of International Application No. PCT/GB2017/053766, filed Dec. 15, 2017, which in turn claims the benefit of and priority to United Kingdom Application Nos. GB1621422.3, filed Dec. 16, 2016 and GB1711923.6, filed Jul. 25, 2017.

The present invention relates to a medical probe for traversing a tract in the body of a human or animal, and which may be a fistula probe for use in treating a fistula. The present invention also relates to a medical probe assembly comprising a medical probe for traversing a tract and a treatment element, and which may be fistula probe assembly comprising a fistula probe and a flexible elongate treatment element. The present invention also relates to a seton assembly for use in treating a tract in the body, which tract may be a fistula, and a method of treating a tract such as a fistula. In particular, but not exclusively, the present invention relates to a fistula probe comprising a deformable member which is inserted into and along a fistula tract.

A fistula is an abnormal passage or tract which occurs between a hollow or tubular organ of a patient and the surface of the body, or between two hollow or tubular organs. These include anal and vaginal fistulae.

An anal fistula is one that develops between the end of the bowel and the skin near the anus. It involves an infection in the anal canal, which presents as an abscess and frequently results in a fistula tract (a tract joining an organ to the skin), which causes recurrent abscesses and chronic sepsis. It has been found to be a disease that impacts on younger people, typically affecting those in the third and fourth decades of life. It necessitates recurrent hospital admissions to treat acute episodes of perianal sepsis, and is a cause of chronic ill health and time off work.

Anal fistulae are thought to develop due to infection in an anal gland, when they are referred to as cryptoglandular fistulae. Cryptoglandular fistulae account for 95% of cases in western populations. Other causes of fistulae include malignant disease of the anorectum, complications of pelvic radiotherapy, obstetric trauma, inflammatory bowel disease, and specific infections including tuberculosis.

In western societies, the annual incidence of cryptoglandular anal fistulae has been found to be between 10 and 23 per 100,000 of the population. In developing parts of the world, the incidence may be higher. For example, it has been reported that 7 per 1000 males in India suffer from anal fistulae. This possibly reflects the high incidence of tuberculosis fistulae occurring in South East Asia.

Surgery is the only cure for fistulae-in-ano, but is associated with high rates of recurrence (reported at 20% to 50%). A large number of surgical techniques are used to treat fistulae, which is testament to the lack of efficacy of any one procedure. Currently, in the National Health Service of the United Kingdom, preferred methods include fistulotomy (cutting open of the fistula), rectal advancement flap (covering the anal opening of the fistula with a flap of normal rectum), anal fistula plug (a collagen plug inserted into the fistula to promote healing), the 'LIFT' procedure (division and ligation of the fistula tract), and cutting 'setons' (non-dissolvable sutures tied around the tract to produce slow division and simultaneous healing).

Setons are devices, usually made from non-dissolvable sutures or drains, which are used in the acute setting to drain a fistula of residual sepsis, and to allow the tract to mature before attempts at surgical cures are made using one of the above techniques. Insertion of a seton involves the use of a malleable probe to define the fistula, the probe being passed from an external opening of the fistula, along the fistula tract, and through an internal opening inside the anal canal. Once the probe has been passed through the tract, it can be used to thread a seton through the tract, which is then secured, usually by tying the seton, so that it can act as a drain.

Because the fistula tract is often tortuous, it can be difficult to negotiate the tract with a straight probe. Care must also be taken not to create a 'false' passage. As a consequence, the malleable probe must be repeatedly inserted into, and retracted from, the fistula tract, and plastically deformed to adopt a shape which is suited for traversing the tract. This procedure is time-consuming and requires a high degree of skill on the part of the medical practitioner. Consequently, such procedures are normally only carried out by a suitably trained surgeon. In addition, the procedure is painful, and so is performed under general anaesthetic as a 'day case' operation. These factors all contribute towards making the procedure expensive.

Attempts have been made to address some of the deficiencies with prior probes and associated procedures for treating fistulae.

One prior fistula probe is disclosed in Chinese Utility Model No. CN-202553908. The fistula probe disclosed in the document comprises a probe tube, and a 'lead-introducing device'. The probe tube comprises a tube body composed of an inner tube and an outer tube. The outer tube is a spring coil, discussed as being 'spirally formed' by a metallic strip, whilst the inner tube is a plastic tube made of a medical plastics material. The probe tube is used for introducing the lead-introducing device into the fistula. The lead-introducing device is a spring coil, discussed as being 'spirally formed' by a metallic strip. The lead-introducing device is introduced into the fistula through the probe tube. A thread can be introduced into the fistula tract using the probe.

The structure of the probe disclosed in CN-202553908 renders it relatively expensive to manufacture. In addition, it is believed that the inner plastic tube of the probe tube, which has a relatively thick wall, will counteract the elasticity of the outer elastic tube, rendering the probe tube as a whole plastically deformable. The probe tube will therefore suffer the same difficulties as those associated with prior, plastically deformable fistula probes discussed above.

The present invention provides a medical probe for traversing a tract in the body of a patient, which may be a body of a human or animal patient. Whilst the medical probe has a particular use in traversing a fistula tract in the body, it may have a use in traversing other tracts in the body, including but not restricted to a tendon or ligament sheath, as well as tracts forming part of the vascular system such as arteries and veins.

According to a first aspect of the present invention, there is provided a medical probe for traversing a tract in a body of a patient, the probe comprising:

an elongate elastically deformable member comprising a helically wound element; and a sheath having an inner surface which contacts an outer surface of the elastically deformable member.

The medical probe may have a particular use in the treatment of a fistula, and may take the form of a fistula probe adapted to traverse a fistula tract.

Reference is made herein to a probe for traversing a tract. It will be understood that references to the probe traversing a tract should be taken to mean that the probe is capable of being inserted into and travelling along at least part of a length of a tract. Typically, the probe will be pushed along the tract by an operator.

The probe of the present invention is elastically deformable, its elastic characteristics being provided by the elastically deformable member. This facilitates movement of the probe along a tract, as the probe can readily elastically deform so as to conform to the shape of the tract (which can be tortuous). In the context particularly of a fistula probe, this addresses the problems with prior, plastically deformable fistula probes, which are substantially rigid and have to be plastically deformed (i.e. bent) in order to traverse the fistula tract.

The sheath, which contacts the outer surface of the elastically deformable member, may prevent body tissue from entering between coils or turns of the helically wound element. This may reduce discomfort to the patient and ease passage of the probe along the tract.

In the particular context of a fistula probe, it is believed that the probe of the present invention can be employed in a procedure that does not require a highly specialised medical practitioner (e.g. a specialist surgeon), and under local anaesthetic, rather than general anaesthetic as with prior probes that are rigid. Such would significantly reduce the costs associated with procedures employing the fistula probe, in comparison to those employing prior probes.

The elastically deformable member may have a first, rest configuration which the member adopts in the absence of an external load or force (of sufficient magnitude). The external load or force may be one that is imparted on the member through contact with a wall of a tract, and/or by an operator of the probe. In the rest configuration, the elastically deformable member may be substantially straight, and/or may adopt a substantially straight position/shape. The elastically deformable member may have a longitudinal axis, and may be capable of being deformed so that a portion or portions of the member are displaced from the axis. The member may be capable of being deformed so that a portion or portions of the member are disposed at a (non-parallel) angle relative to the axis. The angle may be up to at least 90°, may be up to at least 180°, may be up to at least 270°, and may be up to at least 360°. This may allow the member to negotiate a tortuous tract.

The elastically deformable member may be movable to a second configuration on application of an external load or force. A restorative force of the elastically deformable member, which may be a spring force, may act to urge the elastically deformable member to its rest configuration in the absence of such an external load or force. In the second configuration, the elastically deformable member may be bent away from the substantially straight position/shape that it adopts in the rest configuration. The elastically deformable member may be capable of being bent in more than one direction. The elastically deformable member may be capable of being bent at multiple locations which are spaced apart along a length of the member.

The sheath may impart a force on the elastically deformable member which acts to restrict return movement of the member to its first configuration, and/or which may prevent it from fully returning to the first configuration, in the absence of an external load. The sheath may act to partially restrict movement of the elastically deformable member. Such may be due to the way in which the sheath is fitted to the outer surface of the elastically deformable member. The sheath may restrict the movement of the elastically deformable member so that it adopts a third configuration in which the member is not fully in the first configuration. The elastically deformable member may still be deformed when it is in the third configuration. A degree of deformation of the elastically deformable member in the third configuration may be less than in the second configuration. This may provide the fistula probe with a degree of 'imperfect elasticity', Which may assist in traversing a tract. The extent to which the sheath restricts/prevents movement of the elastically deformable member may be determined by factors including: a material of the sheath; a thickness of a wall of the sheath; and inherent resilience of the elastically deformable member.

The elastically deformable member may comprise or take the form of a spring having a plurality of turns or coils. The spring may be a tension spring. The helically wound element may form the spring. The spring may be arranged so that the turns or coils are in abutment, at least in a rest configuration of the elastically deformable member. The helically wound element may be of a metal material, and may be of a stainless steel material. The inherent resilience may be a spring force/inherent tension of the spring.

The sheath may be a substantially tubular member which is adapted to be fitted over the elastically deformable member.

The sheath may be formed from an elongate element which is helically wound on to the elastically deformable member so as to cover the member, and which may be an elongate wrapping element. The elongate element may comprise a tape, strap or strip. Successive turns of the helically wound elongate element may overlap a preceding turn.

The sheath may be deformed into contact with the outer surface of the elastically deformable member, and may be shrunk. The sheath may be of a material which deforms on application of heat, and may shrink. The sheath may therefore be deformed, in particular heat-shrunk, on to the outer surface of the elastically deformable member. The sheath may be located over the outer surface of the elastically deformable member, and heat applied to the sheath to shrink the sheath into contact with the outer surface of the elastically deformable member, and/or into closer contact with the outer surface. The sheath may be of a plastics material. The sheath may be of a polymeric material. Suitable materials for the sheath may include polytetrafluoroethylene (PTFE) and fluorinated ethylene propylene (FEP). PTFE and FEP materials are known to be biocompatible and have relatively low coefficients of friction, the latter facilitating fitting of the sheath to the elastically deformable member and/or passage of the probe along the tract. FEP has a lower melting point than PTFE, and may be better suited to heat-shrinking.

The sheath may extend part way along a length of the elastically deformable member. It is therefore possible that only part of the outer surface of the elastically deformable member is covered by the sheath. The sheath may extend from a leading end or nose of the elastically deformable member and along the member. The sheath may extend along the elastically deformable member and over a trailing end or tail of the member. The probe may comprise a first sheath extending along a first length of the elastically deformable member, and at least one further sheath extending along a second length of the elastically deformable member. The first and second lengths may be spaced apart.

The sheath may cover the entire outer surface of the elastically deformable member. The sheath may extend beyond an end of the elastically deformable member. A portion of the sheath may extend beyond the end of the elastically deformable member, which may be a trailing end or tail of the member. The portion may have an internal diameter which is greater than an effective internal diameter of a portion which is provided in contact with the outer surface of the elastically deformable member.

The probe may comprise, or may be adapted to cooperate with, a treatment element, which may be a flexible elongate treatment element. The probe may be adapted to draw the treatment element into the tract, and then to be released from the treatment element leaving it within the tract. The treatment element, once in place within the tract, may serve for maintaining the tract open. In the particular context of a fistula probe, the treatment element may facilitate one or more of: drainage of the tract, e.g. the draining of pus and/or infectious material from the tract; the supply of treatment materials into the tract; and as a preparatory step to a surgical procedure such as a fistulectomy or fistulotomy. The treatment element may be employed to excise or exteriorise the fistula in a fistulectomy or fistulotomy procedure employing the treatment element. The treatment element may then act as a cutting element, in particular a cutting seton. The treatment element may be coupled to the probe (particularly the deformable member) so that it is drawn into the fistula tract by the probe. The treatment element may be releasably coupled to the probe.

Where the sheath comprises a portion which extends beyond the end of the elastically deformable member, the treatment element may be located within said portion. Said portion may therefore be a treatment element receiving portion. The treatment element may have an external diameter which is less than an internal diameter of said portion. The treatment element may protrude beyond an end of the sheath. This may facilitate gripping or grasping of the treatment element by an operator, so that the sheath can be drawn over the treatment element leaving it in place within the tract. Frictional contact between an internal surface of said portion of the sheath and an external surface of the treatment element may be sufficient to retain the treatment element within said portion during passage of the probe along the tract. Said portion of the sheath may be deformed into contact with at least part of an outer surface of the treatment element, and may be shrunk (e.g. heat shrunk). The sheath may be deformed along its entire length, or a majority of its length.

The treatment element may be hollow and may extend over an outer surface of the elastically deformable member. The treatment element may form the sheath, or at least part of the sheath. The treatment element may be arranged to engage the elastically deformable member in an interference fit. An internal diameter of the treatment element may be smaller than a diameter of the elastically deformable member, which may be an external diameter. This may provide the interference fit. The elastically deformable member may have a first portion of a first diameter, and a second portion of a second diameter, the second diameter being smaller than the first diameter. The elastically deformable member may taper from the first diameter to the second diameter. The treatment element may be arranged to engage the second portion of the elastically deformable member, and may be arranged so that it does not extend over or on to the first portion. An external diameter of the treatment element may be substantially the same as the first diameter, at least prior to location of the treatment element over the second portion. The probe may comprise the hollow treatment element, and a further treatment element which may be a flexible elongate treatment element. The further treatment element may be a seton and may be a suture, such as a surgical thread. The further treatment element may be adapted to be coupled to the elastically deformable member via the hollow treatment element. The further treatment element may be adapted to be located within the hollow treatment element. The further treatment element may be adapted to extend within an internal cavity defined by the elastically deformable member. The further treatment element may be adapted to be located between an inner surface of the hollow treatment element and an outer surface of the elastically deformable member. This may serve for capturing the further treatment element so that it can be drawn into the tract with the elastically deformable member.

The treatment element may be a seton. A seton may be defined as being a surgical element for use in treatment of a tract, in particular a fistula. The seton may be a suture, and may be a surgical thread.

The treatment element, in particular the seton, may be tubular. The treatment element may have first and second tubular ends. Where the entire treatment element is tubular, a passage may extend along a length of the treatment element between the first and second open ends. The probe may comprise a support element, which may be a plug, adapted to be located within a tubular end of the seton. The support element may support the seton internally, particularly in a situation where the sheath is deformed into contact with the seton. This may resist collapse of the tubular seton, promoting frictional contact between the sheath and the seton, and so gripping of the seton by the sheath. Following location of the seton within a tract, the sheath and the seton may be severed at a location which is between the support element and a trailing end of the sheath. The support element may have an external diameter which is larger than an internal diameter of the seton. This may act to deform the seton outwardly, promoting contact with the sheath.

The treatment element may be of an elastomeric material. Suitable materials included inert silicone elastomers such as those commercially available from Dow Corning Corporation in the USA under the SILASTIC Trade Mark.

The probe may have a first end and a second end. The first end may be closed. The second end may be open. The first end may form a leading end of the probe. The second end may form a trailing end of the probe. The sheath may form the first end of the probe. The sheath may form the second end of the probe.

The probe may have a leading end, head or tip which is adapted to be inserted into a tract. The probe may have a trailing end or tail. The leading end may be tapered or otherwise shaped to facilitate insertion of the probe into the tract and/or passage of the probe along the tract. The probe may taper from a first outside diameter of the sheath provided around the elastically deformable member, to a second smaller diameter at a lead-most part or portion of the leading end.

The leading end may be defined by an end component which is coupled to the elastically deformable member. The sheath may extend over the leading end component. The sheath may form or comprise the leading end component. The leading end component may have a shape selected from the group comprising: spherical; hemispherical; conical; truncated conical; rounded; and generally bullet-shaped.

The leading end may be formed by the elastically deformable member, in particular by the helically wound element. This may be achieved by tapering an end of the member/element.

The fistula probe may comprise a coupling feature, for coupling a further component to the probe. The further component may be selected from the group comprising: a cleaning tool; a treatment element such as a flexible elongate treatment element, in particular a seton; and a suture or other medical element. The cleaning tool may comprise a cleaning element such as a brush, and a flexible elongate coupling element such as a wire, cable, thread or suture which can be secured to the coupling feature. The coupling feature may be provided on or by the elastically deformable member. The coupling feature may be an eyelet of or on the elastically deformable member, which may be formed by the helically wound element e.g. by a loop or coil of the element.

According to a second aspect of the present invention, there is provided a medical probe fix traversing a tract in a body of a patient, the probe comprising:

an elongate elastically deformable member comprising a helically wound element, the elastically deformable member having a leading end and a trailing end;

a first, hollow treatment element located around an outer surface of the elastically deformable member and extending over the trailing end, the first treatment element having an inner surface which contacts an outer surface of the elastically deformable member; and a further treatment element located within the first elongate treatment element, in which the further treatment element is coupled to the elastically deformable member via the first treatment element.

The first, hollow treatment element may be a flexible elongate treatment element. The further treatment element may be a flexible elongate treatment element. The further treatment element may be for performing a medical procedure in the body.

Further features of the medical probe of the second aspect of the invention may be derived from the text set out elsewhere in this document, in particular that relating to the first aspect of the invention.

According to a third aspect of the present invention, there is provided a medical probe assembly comprising the medical probe of the first or second aspect of the invention and a treatment element, which may be a flexible elongate treatment element, coupled to the probe.

Further features of the medical probe of the third aspect of the invention may be derived from the text set elsewhere in this document, in particular that relating to the first or second aspect of the invention. Further features of the treatment element may be derived from the text set out elsewhere in this document, in particular that relating to the first or second aspect of the invention.

The assembly may comprise a connecting element for joining a first end of the treatment element to a second end of the treatment element. This may serve to retain the treatment element in place within the tract, by forming the treatment element into a loop and coupling the ends together using the connecting element.

Where the treatment element is tubular and/or comprises first and second tubular ends, the connecting element may be insertable into the first and second ends to join the ends together. The connecting element may engage the treatment element in an interference fit. An external diameter of the connecting element may be greater than an internal diameter of the treatment element, so that the treatment element is deformed during insertion of the connecting element. Inherent flexibility of the treatment element may facilitate such coupling. A first portion of the connecting element may be locatable within the first end of the treatment element, and a second portion of the connecting element may be locatable within the second end of the treatment element. The connecting element may be: insertable into one of the first and second ends; a portion of the treatment element at the other one of the first and second ends adapted to be rolled back and the connecting element insertable in said other end; and the portion that has been rolled back adapted to then be rolled forward over the portion of the connecting element located in said other end. The portion that is rolled forward may extend over an entire length of the connecting element, and so may extend over said one of the first and second ends. An adhesive may be used to secure the connecting element to one or both of the first and second ends of the treatment element.

The connecting element may be a plug or plug-like element. The connecting element may comprise one or more anchoring feature for anchoring the connecting element to the flexible elongate treatment element. The connecting element may comprise at least one first anchoring element for anchoring the element to the first end of the treatment element, and at least one second anchoring element for anchoring the element to the second end of the treatment element. The anchoring element may be a protrusion. The protrusion may be a barb, hook, tooth or the like.

According to a fourth aspect of the present invention, there is provided a seton assembly for use in treating a tract in a body of a patient, the seton assembly comprising:

a flexible seton having a first open end and a second open end; and a connecting element which is insertable into the first and second ends to join the ends together;

in which:

the connecting element is insertable into one of the first and second ends;

a portion of the flexible elongate treatment element at the other one of the first and second ends is adapted to be rolled back and the connecting element insertable in said other end; and the portion that has been rolled back is adapted to then be rolled forward over the portion of the connecting element located in said other end.

The seton may have a particular use in the treatment of a fistula.

The seton may be tubular, having a passage extending between its first and second ends. By joining the first and second ends together, the seton may be formed into a loop, with a portion of the seton residing within a tract. The portion remaining in the tract may be for maintaining the tract open, and/or for carrying out a step in a medical treatment.

The present invention may also relate to a method of treating a tract in a body of a patient employing the seton assembly of the third aspect of the invention.

Further features of the seton may be derived from the text set out elsewhere in this document, in particular the text set out above relating to the first, second and/or third aspect of the invention.

According to a fifth aspect of the present invention, there is provided a method of treating a tract in a body of a patient, comprising the steps of:

coupling a first end of a treatment element to a medical probe according to the first or second aspect of the invention;

inserting a leading end of the probe into a first opening of a tract trailing the treatment element;

manoeuvring the probe along the tract and out of a second opening of the tract;

removing the probe from the tract through the second opening;

releasing the treatment element from the probe;

removing the probe from the body of the patient leaving the treatment element in place within the tract, a first portion of the treatment element comprising the first end extending from the second opening of the tract, and a second portion of the treatment element comprising a second end extending from the first opening of the tract; and coupling the first end of the treatment element to the second end to form a loop and thereby retain the treatment element within the tract.

The method may be a method of treating a fistula. The treatment element may be a flexible elongate treatment element.

The first opening of the tract may be an exterior opening, on or in the skin of a patient. The second opening may be an interior opening, which may communicate with an interior of the body, in particular a hollow or tubular organ.

The first and second openings of the tract may both be interior openings, which may communicate with an interior of the body. The first opening may communicate with a first hollow or tubular organ, and the second opening with a second hollow or tubular organ.

The method may comprise cutting the treatment element to a desired length following location of the treatment element within the tract. This may involve cutting the treatment element at a location which is spaced from one (or both) of the first and second ends.

The treatment element may be hollow, and may be coupled to the fistula probe by locating the treatment element over the probe. The method may comprise coupling a further treatment element, which may be flexible elongate treatment element, to the probe using the hollow treatment element. The further treatment element may be located within the hollow treatment element. The further treatment element may be a seton, and may be a suture. The step of coupling the first end of the hollow treatment element to the second end to form a loop may comprise tying ends of the suture together, to hold the hollow treatment element in the loop shape. The method may comprise subsequently manoeuvring a knot used to tie ends of the suture together to a location where it is disposed within the hollow treatment element.

In a variation on the method, the treatment element may remain coupled to the probe and the probe used to manipulate the treatment element to perform a medical procedure in or through the tract. The method may comprise drawing the treatment element through the tract using the probe, for example from the first tract opening to the second tract opening and out of the tract.

Further features of the method of the fifth aspect of the invention may be derived from the text set out elsewhere in this document, in particular from the text relating to any one or more of the first to fourth aspects of the invention.

Embodiments of the present invention will now be described, with reference to the accompanying drawings, in which:

FIG. 2 is a side view of a medical probe in accordance with an embodiment of the present invention;

FIG. 3 is a longitudinal sectional view of the probe shown in FIG. 2;

FIG. 5 is a side view of a medical probe in accordance with another embodiment of the present invention;

FIG. 6 is a longitudinal sectional view of the probe shown in FIG. 5;

FIG. 7 is a side view of a medical probe in accordance with a further embodiment of the present invention;

FIG. 8 is a longitudinal sectional view of the probe shown in FIG. 7;

FIG. 17 is an enlarged side view of the probe shown in FIG. 15, illustrating an alternative method of coupling a treatment element to an elongate elastically deformable member of the probe.

The present invention provides a medical probe for traversing a tract in the body of a patient, which may be a body of a human or animal patient. Whilst the medical probe has a particular use in traversing a fistula tract in the body, it may have a use in traversing other tracts in the body, including but not restricted to a tendon or ligament sheath, as well as tracts forming part of the vascular system such as arteries and veins.

Figure 1:
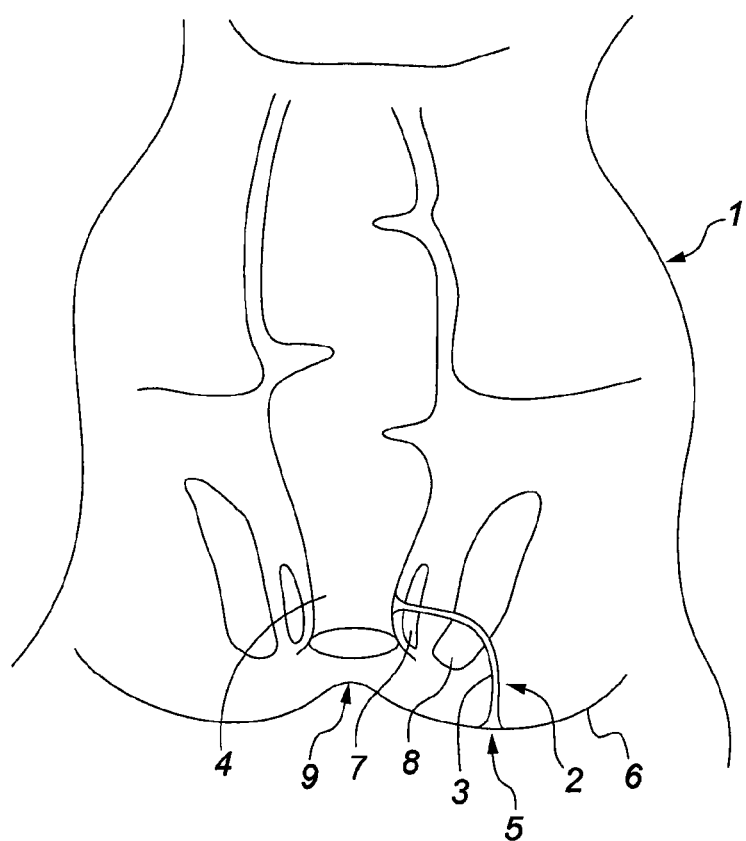
FIG. 1 is a schematic cross-sectional illustration of an anal region of a patient suffering an anal fistula, the fistula forming a tract in the body of the patient.

Accordingly, and turning firstly to FIG. 1, there is shown a schematic view of an anal region 1 of a patient having an anal fistula, indicated generally by reference numeral 2. The fistula 2 comprises a tract 3 extending between the anal canal 4 and an exterior location 5 on the skin 6 of the patient, extending through the internal and external sphincter muscles 7 and 8. Fistula tracts typically have a width of around 2 mm, although this of course varies from patient to patient.

Turning now to FIG. 2, there is shown a side view of a medical probe in accordance with an embodiment of the present invention, the probe indicated generally by reference numeral 10. In the illustrated embodiment, which is involved in the treatment of a fistula 2, the probe 10 takes the form of a fistula probe. The probe 10 is also shown in the longitudinal sectional view of FIG. 3.

Figure 4:
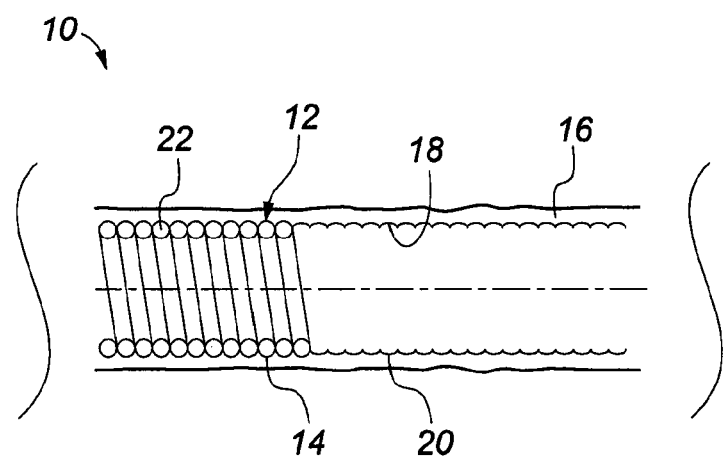
FIG. 4 is an enlarged longitudinal sectional view showing parts of an elongate elastically deformable member and a sheath of the probe shown in FIG. 2.

The probe 10 comprises an elongate elastically deformable member 12, which comprises a helically wound element 14, also shown in the enlarged view of FIG. 4. The probe 10 also comprises a sheath 16 having an inner surface 18 which contacts an outer surface 20 of the elongate elastically deformable element 12.

Figure 4A:
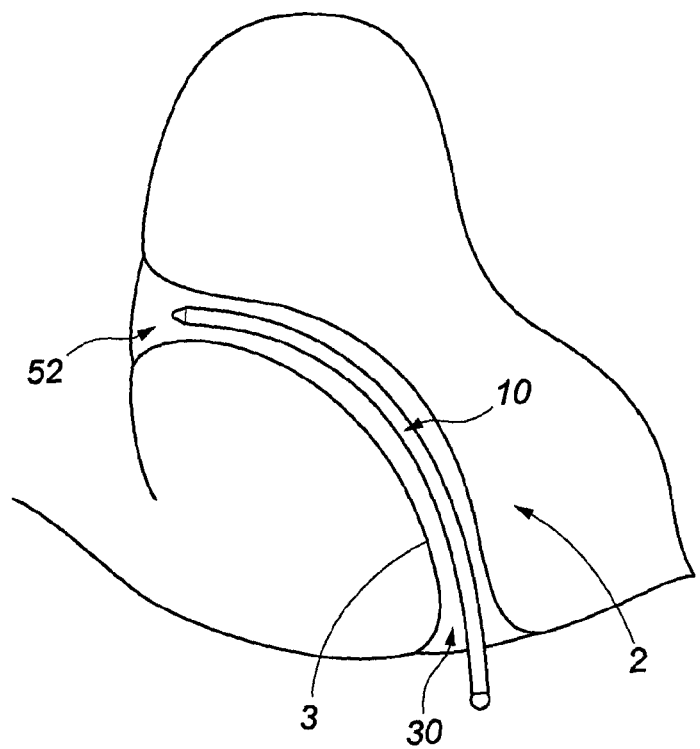
FIG. 4A is an enlarged view of the fistula shown in FIG. 1, showing the probe of FIG. 2 located within the tract.

The probe 10 is elastically deformable, its elastic characteristics being provided by the elastically deformable member 12. This facilitates movement of the probe 10 along the fistula tract 3, as the probe 10 can readily elastically deform so as to conform to the tortuous shape of the tract 3. This is best shown in FIG. 4A, which shows the probe 10 located within the tract 3. In addition, the sheath 16, which contacts the outer surface 20 of the elastically deformable member 12, prevents body tissue from entering between coils or turns 22 of the helically wound element 14. This reduces discomfort to the patient and eases passage of the probe 10 along the fistula tract.

The elastically deformable member 12 has a first, rest configuration which it adopts in the absence of an external load or force, the member shown in FIG. 2 in its rest configuration. The elastically deformable member 12 is moveable to a second configuration on application of an external load or force which may be imparted upon the member 12 during passage along the fistula tract 3 and/or by a medical practitioner. This is illustrated in FIG. 4A, which shows the probe 10 in a second, bent configuration, following insertion into the tract 3.

The sheath 16 imparts a force on the elastically deformable member 12 which acts to restrict return movement of the member 12 to its first configuration to a certain extent, in the absence of an external load. Such may be due to the way in which the sheath 16 is fitted to the outer surface 20 of the elastically deformable member 12. The sheath 16 may be arranged so that it does not substantially restrict return movement of the member 12 to its first configuration. Optionally however, the sheath 16 can be arranged to restrict return movement of the elastically deformable member 12 to the first configuration, so that it adopts a third configuration in which it still be deformed (i.e. bent). In this case, a degree of deformation of the elastically deformable member 12 in the third configuration is less than in the second configuration. This may provide the fistula probe 10 with a degree of 'imperfect elasticity', which may assist in traversing the fistula tract 3. The extent to which the sheath 20 restricts/prevents movement of the elastically deformable member 12 may be determined by factors including: a material of the sheath; a thickness of a wall of the sheath; and inherent resilience of the elastically deformable member.

The elastically deformable member 12 has a longitudinal axis L, and may be capable of being deformed so that a portion or portions of the member are displaced from the axis. The deformable member 12 may be capable of being deformed so that a portion or portions of the member are disposed at a (non-parallel) angle relative to the axis L. The angle may be up to at least 90% may be up to at least 180°, may be up to at least 270°, and may be up to at least 360°. This may allow the deformable member 12 to be significantly deformed, including to be looped back on or over itself, which may facilitate negotiation of a particularly tortuous tract.

In the illustrated embodiment, the elastically deformable member 12 takes the form of a spring having a plurality of turns or coils 22 (FIG. 4). The spring can have any suitable diameter, but typically will have a diameter in the region of 1.5 mm, so that it is capable of passing along fistula tracts which typically have a width of 2 mm, as discussed above. It will be understood that the probe may be of different dimensions depending upon its intended use, and in particular a diameter of the tract that it is to traverse. A pitch of the spring 12 is selected so that each coil 22 is in abutment with an adjacent coil or coils, in the rest configuration of the spring. In this way, there are no significant gaps between adjacent coils 22 of the spring 12 when it is in its rest configuration. Suitably, the helically wound element 14 forming the spring 12 is of a metal material, in particular a stainless steel material, which is known as being suitable for medical uses.

The sheath 16 is a substantially tubular member which is fitted over the spring 12. In the illustrated embodiment, the tubular sheath 16 covers the entire outer surface 20 of the spring 12, save for a coupling feature 24 defined by the spring 12, and which will be described in more detail below. The sheath is typically relatively thin-walled, and may have a wall thickness of 0.1 mm or less. The tubular sheath 16 defines the inner surface 18 which contacts the outer surface 20 of the spring 12. The tubular sheath 16 is deformed into contact with the outer surface 20 of the spring 12, suitably by heat-shrinking the sheath into contact with the outer surface 20. To this end, the sheath is suitably of a plastics material, particularly a polymeric material, and preferably polytetrafluoroethylene (PTFE) or fluorinated ethylene propylene (PEP). MIT and PEP are known to be biocompatible and have relatively low coefficients of friction, the latter facilitating fitting of the tubular sheath 16 to the spring 12, as well as passage of the probe 10 along the tract 3. PEP may be particularly suitable for heat-shrinking, as it has a lower melting point than PTFE.

The probe 10 has a leading end 26 and a trailing end, the leading end 26 adapted to be inserted into an opening of the fistula tract 3, in this case an exterior opening 30 (FIG. 4A). The leading end 26 is suitably tapered or otherwise shaped to facilitate insertion of the probe 10 into the tract 3, and passage of the probe along the tract. The probe tapers from a first outside diameter $D_1$ to a second smaller diameter $D_2$ at a lead-most part 32 of the leading end 26.

The tapered leading end 26 may be provided in a number of ways. In a first option, the sheath 12 itself forms the leading end 26, by suitable heat treatment, for example using a soldering iron or by pressing the sheath 16 (following heat-shrinking onto the spring 12) against a hot plate (not shown). Alternatively and as shown in FIG. 3, an end 34 of the spring 12 may be tapered, by suitable shaping of coils 22 of the spring, to define the tapered leading end 26. The sheath 16 is then heat shrunk around the spring, including its end 34.

FIG. 5 is a side view of a medical probe in accordance with an alternative embodiment of the present invention, indicated generally by numeral 100, and which is again provided as a fistula probe. Like components of the probe 100 with the probe 10 of FIGS. 2 and 3 share the same reference numerals, incremented by 100. Only the substantial differences between the probe 100 of FIG. 5 and the probe 10 of FIG. 2 will be described in detail.

The probe 100 of FIG. 5 illustrates an alternative method of forming a leading end 126. In this embodiment, a separate end component 36 is coupled to a spring 112 of the probe 100, the end component 36 being shaped so as to form the tapered leading end 126. The end component 36 may be of any suitable material including plastics and metals, and can have a number of different shapes. In the illustrated embodiment, the end component is hemispherical. The end component 36 can also be secured in a number of different ways. In one example, the end component 36 is secured to the spring 112 using an adhesive. A sheath 116 may extend around the end component 36 to provide further securement. Alternatively, the sheath 116 may extend up to a junction 38 between the end component 36 and the spring 112.

Alternative shapes for the end component 36 include spherical, conical, truncated conical, rounded and generally bullet-shaped or bulleted. In addition, the end component 36 may be located in position at the leading end 126 by inserting part of the end component 36 into a bore 40 of the spring 112. For example, the end component 36 may have a projection (not shown) which is received in an end of the bore 40 for locating it in position.

Returning to FIG. 2, the fistula probe 10 (and indeed the probe 100) may be adapted to cooperate with, and may comprise, a treatment element 42, suitably in the form of a flexible elongate treatment element. In the illustrated embodiments, the flexible elongate treatment element 42 is a seton. The seton 42 can take different forms, but in the embodiment of FIG. 2, comprises a surgical thread, cord or alternatively a single filament. The seton 42 is secured to the probe 10 via the coupling feature 24, which in this embodiment takes the form of an eyelet. The probe 10 draws the seton 42 into the fistula tract 3, and can then be released from the seton 42 leaving it in place within the tract 3. The seton 42, once in place within the tract 3, may serve for maintaining the tract open. This may facilitate one or more of: drainage of the tract; the supply of treatment materials into the tract; and may provide a preparatory step to a surgical procedure to treat the fistula. Optionally, the seton 42 is a cutting seton which is formed into a loop and tensioned to apply pressure to surrounding tissue, so as to slowly cut through the body tissue and exteriorise the fistula tract 3.

As also shown in FIG. 2, the probe 10 can optionally include, or cooperate with, a cleaning tool 44. The cleaning tool 44 can take many forms, but in the illustrated embodiment takes the form of a brush. The brush 44 may be attached to the probe 10 via the seton 42, which is secured to the eyelet 24. The brush 44 may be used to clean the tract 3, in particular to remove infected material, puss, and/or epithelialised tissue. The eyelet 24 may be provided separately and secured to the spring 12, such as using a suitable adhesive. Alternatively, a coil or coils (not shown) of the spring 12 may be shaped (e.g. twisted) away from a main part of the spring to define the eyelet 24.

Turning now to FIG. 7, there is shown a medical probe in accordance with another embodiment of the present invention, the probe indicated generally by reference numeral 200, again provided as a fistula probe. Like components of the probe 200 with the probe 100 of FIG. 5, or the probe 10 of FIG. 2, share the same reference numerals incremented by 200 or 100, as appropriate. Again, only the substantial differences between the probe 200 and the probes 10, 100 will be described in detail.

The probe 200 shown in FIG. 7 is essentially of similar construction to the probe 10 shown in FIG. 2, save that a sheath 216 extends beyond an end of a spring 212 of the probe, which is shown in the longitudinal sectional view of FIG. 8, an end 44 of the spring 212 being shown in the drawing.

One difference between the probe 200 shown in FIG. 7 and those of FIGS. 2 and 5 are that the probe 200 comprises or is employed with a different type of seton, the seton indicated by reference numeral 242. In this embodiment, the seton 242 is tubular along its entire length, and typically formed of an elastomeric material. The elastomeric material may suitably be an inert silicone elastomer, such as that commercially available from Dow Corning Corporation in the USA under the SILASTIC trade mark. An internal diameter of the sheath 216 is selected to be larger than an internal diameter of the tubular seton 242. In this way, the seton 242 can be located within the second portion 48 of the sheath, which effectively acts as a tail to the probe 200.

In this embodiment, the sheath 216 is again heat-shrunk onto the spring 12. Heat is only applied to a first portion 46 of the sheath 216 which extends along (and so covers) the spring 212, and a short distance along a length of the seton 242. This acts to shrink the sheath 216 into close contact with the spring 212, but also into contact with the seton 242, to grip and so retain the seton. A second portion 48 of the sheath 216, which covers a main part of the seton 242, remains substantially or entirely undeformed. The second portion 48 thus has a larger internal diameter than the effective internal diameter of the first portion 46, which has been heat-shrunk onto the spring 212 and part of the seton 242. In a variation on this embodiment, the sheath 216 may be heat-shrunk along its entire length, to grip the seton 242 along the entire length of the portion of the sheath which receives the seton.

In use, a leading end 226 of the probe 200 is inserted into and along the fistula tract 3, the second portion (or tail) 48 of the sheath 216 carrying the tubular seton 242 into the tract. The leading end 226 is passed out of the tract 3 through an interior opening 52 and withdrawn through the anal canal 4, drawing a leading end 50 of the seton 242 out of the tract 3. The sheath 212 can be released from the seton 242, by grasping a trailing end 54 of the seton 242 (positioned outside of the body), and then pulling the probe 200 to slide the second portion 48 of the sheath 212 over the seton 242.

The probe 200 of FIG. 7 is shown incorporating a coupling feature, which once again may take the form of an eyelet 24. The eyelet 24 may be employed for coupling an alternative seton, such as the seton 42 shown in FIG. 2, to the probe. It will be understood that this would typically need to be carried out prior to positioning the sheath 216 over the spring 212 and heat-shrinking the sheath. Alternatively, the coupling eyelet may be dispensed with.

In variations on the embodiment illustrated in FIG. 7, the seton 242 may have a different structure. For example, the seton may have a solid cross-section, or may be substantially solid with open leading and trailing ends 50, 54.

Figure 9:
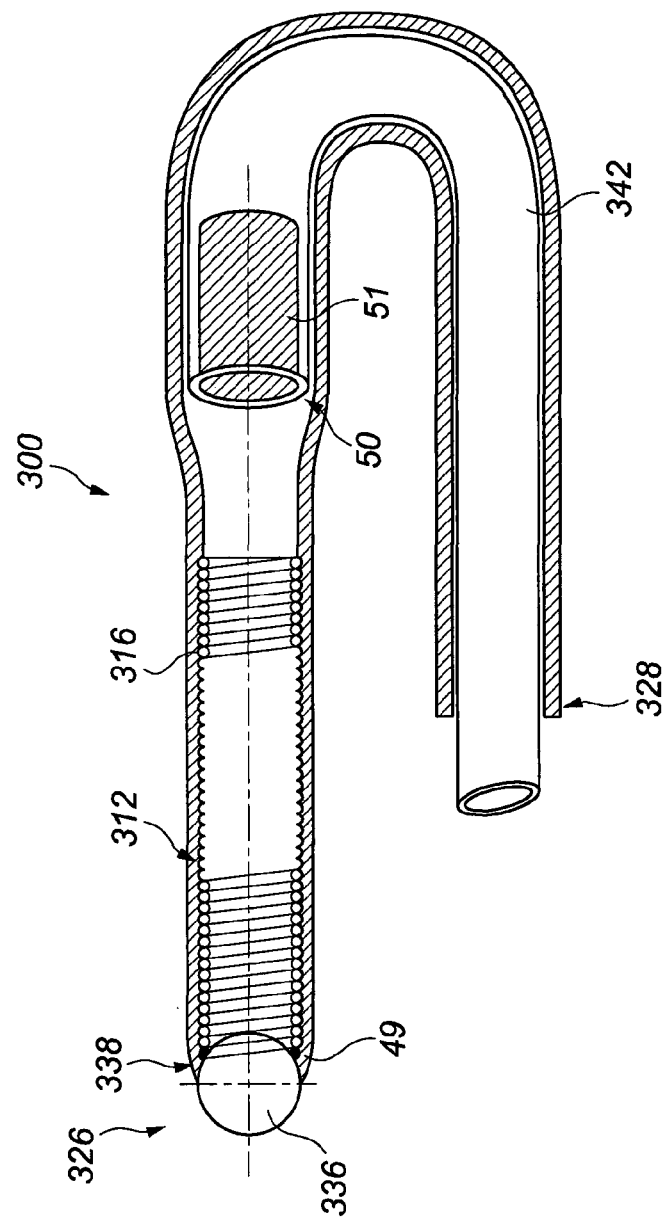
FIG. 9 is a side view of a medical probe in accordance with a further embodiment of the present invention.

Turning now to FIG. 9, there is shown a medical probe in accordance with another embodiment of the present invention, the probe indicated generally by reference numeral 300, and again provided as a fistula probe. Like components of the probe 300 with the probes 10, 100 and 200 of FIGS. 2, 5 and 7 share the same reference numerals incremented by 300, 200 or 100, as appropriate. Again, only the substantial differences between the probe 300 and the probes 10, 100 and 200 will be described in detail.

The probe 300 shown in FIG. 9 is of similar construction to the probe 200 shown in FIG. 7, comprising a spring 312 and a sheath 316 which receives a tubular seton 342, that again may be of a silicone elastomer material. The probe 300 comprises a different leading end 326, having a spherical end component 336, typically in the form of a ball bearing. The ball bearing 336 is typically coupled to the spring 312 using an adhesive, illustrated at 49 in the drawing, the sheath 316 extending up and over the a junction 338 between the ball 336 and the spring 312.

The probe 300 also comprises a support element 51, in the form of a plug, which is adapted to be located within a tubular leading end 50 of the seton 342. The plug 51 supports the seton 342 internally, where the sheath 316 is deformed into contact with it. This resists collapse of the tubular seton 342, promoting frictional contact between the sheath 316 and the seton 342, and so gripping of the seton by the sheath. Following location of the seton 342 within the fistula tract 3, the sheath 316 and the seton 342 may be severed at a location which is between the plug 51 and a trailing end 328 of the sheath 316. The plug 51 typically has an external diameter which is larger than an internal diameter of the seton 342. This acts to deform the seton 342 outwardly, promoting contact with the sheath 316.

In all of the embodiments described above, the seton, once located within the fistula tract, may be formed into a loop and secured in place. This may be achieved by tying a part of the seton protruding from the exterior opening of the tract to a part protruding from the interior opening, suitably using a knot. Alternatively, and where the seton is formed from a suitable material, the parts of the seton may be fused together, e.g. by the application of heat. A further alternative option will be described with reference to FIGS. 10 to 14.

Figure 10:
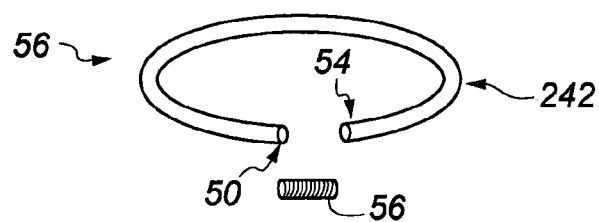
FIG. 10 is a perspective view of a seton assembly in accordance with an embodiment of the present invention.

Thus turning now to FIG. 10, the flexible tubular seton 242 is shown in more detail. It will be understood from the foregoing description that the seton 342 is of like construction, and so that the following applies equally to the seton 342. Whilst the seton 242 may form part of, or be used with, any of the probes 10, 100, 200 and 300 described above, the seton may form part of a seton assembly for use in treating a tract (in particular a fistula) which has a use without the probes disclosed herein. The following discussion therefore applies both to a seton forming part of the disclosed probes 10, 100, 200 and 300 (or which can be used with them), or which can be used separately.

Thus FIG. 10 shows a seton assembly 56 which comprises the seton 242 and a connecting element 56. The connecting element is insertable into first and second ends of the seton 242, which in this case are the leading end 50 and the trailing end 54. This is best shown in the enlarged schematic view of FIG. 10, which shows the connecting element 56 located in the trailing end 54 of the seton 242. The connecting element 56 takes the general form of a plug or plug-like element. The connecting element 56 may provide an interference fit within the ends 50, 54 of the seton 242, suitably by providing the plug 56 with a larger external diameter than an internal diameter of the seton 242.

The connecting element 56 is suitably secured using an adhesive which, where the seton 242 is of a silicone elastomer (such as SILASTIC™) material, may be a dedicated silicone elastomer adhesive. The seton 242 is shown formed into a loop, which is the shape that it would adopt following introduction into the fistula tract 3 using a fistula probe, and withdrawal of the leading end 50 down the anal canal 4 and through the anus 9 of the patient.

Figure 11:
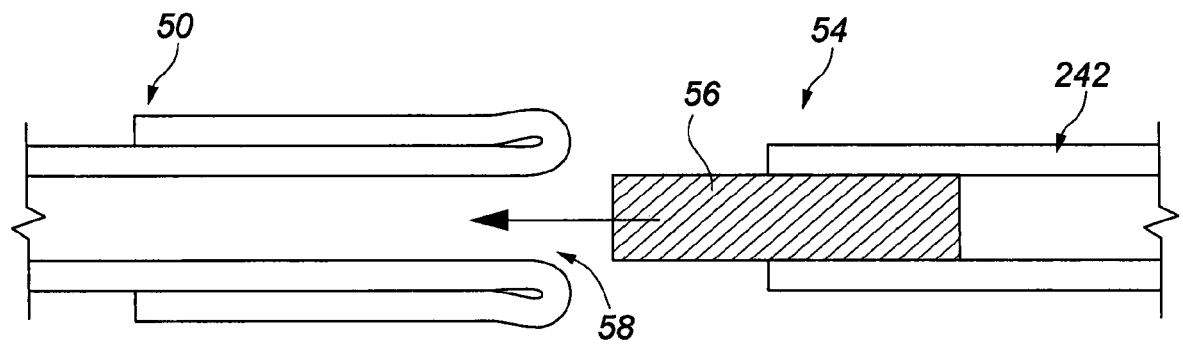
FIGS. 11 to 14 are enlarged schematic sectional views of the seton assembly of FIG. 10, illustrating steps in a method of treatment of a tract employing the seton assembly.
Figure 12:
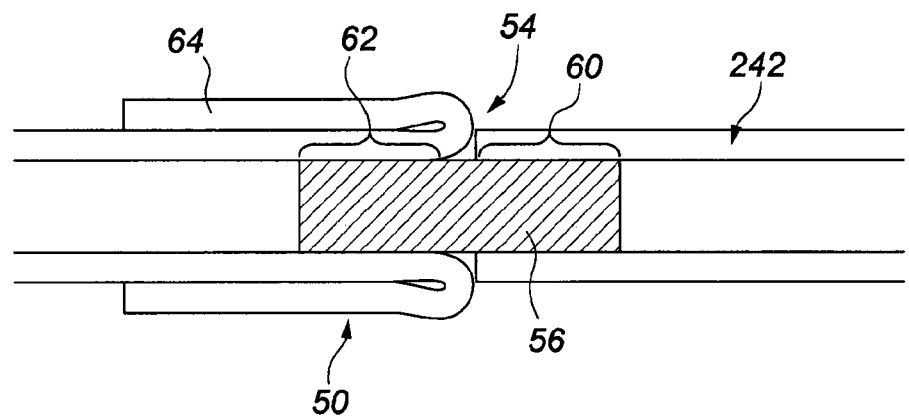

As shown in FIG. 11, the natural flexibility and resilience of the silicone elastomer material forming the seton 242 enables the leading end 50 to be folded back upon itself, so that the connecting element 56 can be inserted into an opening 58 which is then formed. Again, a suitable adhesive may be used to secure the connecting element 56 within the leading end 50 of the seton 242. This is shown in FIG. 12, where a first portion 60 of the connecting element 56 is located within the trailing end 54 of the seton 242, and a second portion 62 of the connecting element 56 is located in the leading end 50.

Figure 13:
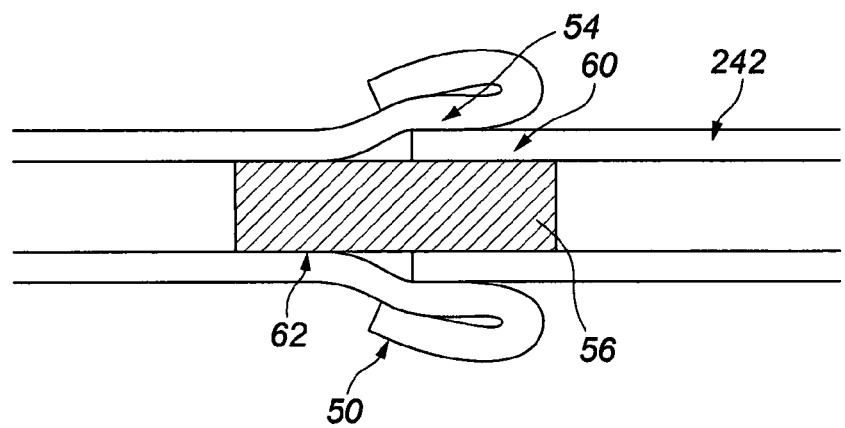
Figure 14:
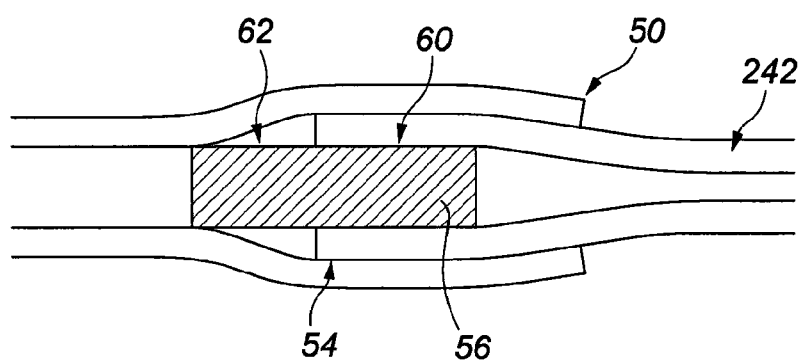

A portion 64 of the seton 242 at the leading end 50 which has been rolled back is then folded back over the first portion 60 of the connecting element 56, as shown in FIG. 13. This continues until the portion 64 that has been rolled back has been frilly extended, as shown in FIG. 14, where it extends beyond the trailing end 54 of the seton 242 and the connecting element 56.

The connecting element 56 may comprise anchoring elements for anchoring it to the seton 242. For example, the connecting element 56 may comprise barbs or teeth (not shown) which extend from a main body of the element, for engaging the seton 242.

Figure 15:
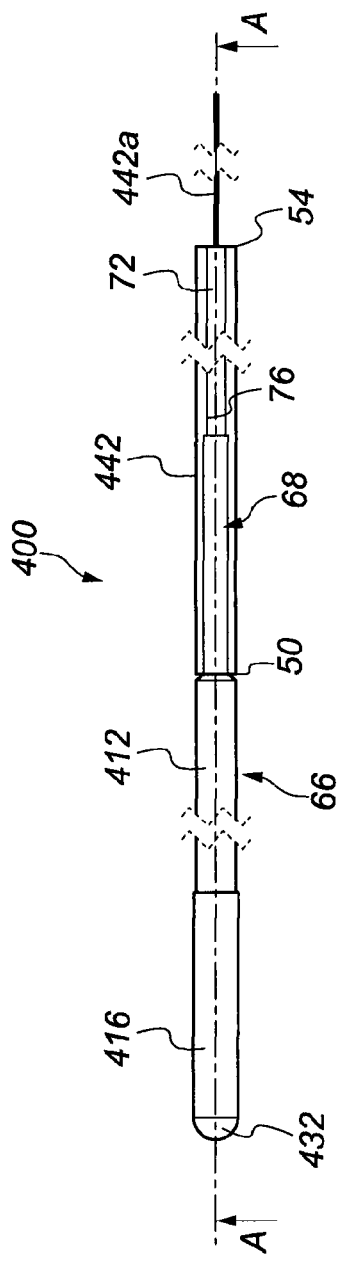
FIG. 15 is a side view of a medical probe in accordance with a further embodiment of the present invention.
Figure 16:
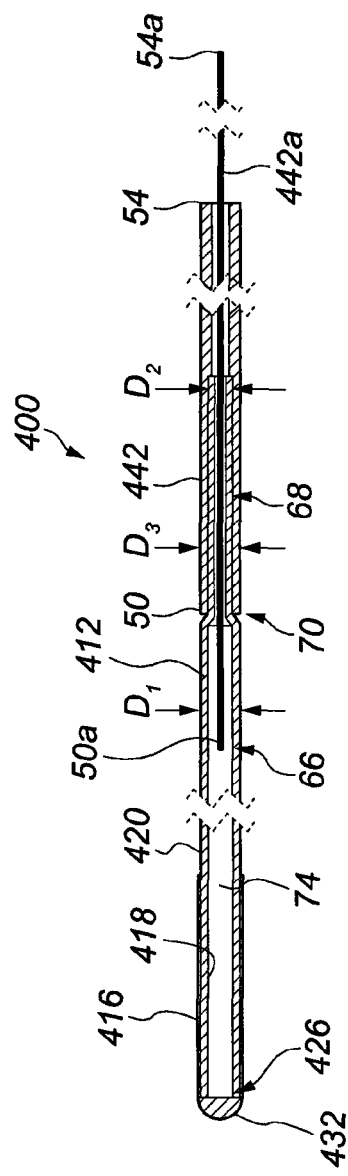
FIG. 16 is a view of the probe shown in FIG. 15, sectioned about line A-A.

Turning now to FIG. 15, there is shown a side view of a medical probe in accordance with a further embodiment of the present invention, the probe indicated generally by reference numeral 400, and again provided as a fistula probe. The probe 400 is also shown in FIG. 16, sectioned about line A-A in FIG. 15. Like components of the probe 400 with the probes 10, 100, 200 and 300 of FIGS. 2, 5, 7 and 9 share the same reference numerals incremented by 400, 300, 200 or 100, as appropriate. Again, only the substantial differences between the probe 400 and the probes 10, 100, 200 and 300 will be described in detail.

The probe 400 comprises an elongate elastically deformable member in the form of a spring 412, which again comprises a helically wound element. The probe 400 also comprises a sheath 416 having an inner surface 418 which contacts an outer surface 420 of the spring 412. In this embodiment, the sheath 416 extends from a leading end 426 of the spring 412 part way along a length of the spring, and assists in insertion of the probe 400 into the fistula tract 3. The sheath 416 may extend any desired distance along a length of the spring 412. In the illustrated embodiment, the sheath 416 extends only a short distance (typically between 0.5 cm and 3 cm) along the length of the spring 412. A lead-most part 432 of the sheath 416 is rounded or bulleted to facilitate insertion and passage along the tract 3, in the fashion described above, although any of the other techniques disclosed herein may be employed to form a tapered nose on the probe.

The probe 400 also comprises a treatment element, suitably a hollow flexible elongate treatment element in the form of a hollow seton 442. Again, the seton 442 may be of a silicone elastomer or other suitable material. The seton 442 extends over the outer surface 420 of the spring 412, and may effectively form part of a sheath of the probe. As will be understood from the drawing, the sheath 416, and the sheath formed by the seton 442, are separate and spaced apart. The seton 442 is arranged to engage the spring 412 in an interference fit, suitably by providing the seton with an internal diameter which is smaller than an external diameter of the spring.

As best shown in FIG. 16, the spring 412 has a first portion 66 which is of a first diameter $D_1$, and a second portion 68 of a second diameter $D_2$, the second diameter being smaller than the first diameter. The spring 412 tapers from the first diameter $D_1$ to the second diameter $D_2$ at an intersection region 70. The hollow seton 442 is arranged to engage the second portion 68 of the spring 412, and is arranged so that it does not extend over the intersection region 70 and on to the first portion 66. As can be seen from the drawings, an external diameter $D_3$ of the seton 442 is substantially the same as (and optionally the same as) the first diameter $D_1$, at least prior to location of the seton over the second portion 68 of the spring 412. In this way, any ledge or shelf between the first portion 66 of the spring 412 and a leading end 50 of the seton 442 is minimised. This may facilitate entry of the probe 400 into the tract 3, and passage along the tract.

The probe 400 also comprises a further treatment element, suitably a flexible elongate treatment element, which is again a seton but which takes the form of a suture 442a, such as a surgical thread. The suture 442a is adapted to be coupled to the spring 412 via the hollow seton 442. This is achieved by locating the suture 442a within an internal cavity 72 defined by the seton 442, and then either: passing the suture 442a into and along an internal cavity 74 defined by the spring 412 (as shown in FIG. 16); or trapping the suture 442a between an inner surface 76 of the hollow seton 442 and the outer surface 420 of the spring 412 in the region of the second portion 68 (as shown in FIG. 17). Either method serves for capturing the suture 442a so that it can be drawn into the fistula tract 3 with the spring 412.

Once located within the fistula tract 3, the hollow seton 442, with the suture 442a located within it, can be separated from the spring 412 leaving them in place within the tract. An interference fit between the hollow seton 442 and the reduced diameter portion 68 of the spring 412 is such that there is sufficient friction to draw the seton into the tract 3, but the fit still allows easy separation from the spring 412 when required. This is achieved simply by holding on to a trailing end 54 of the seton 442 which protrudes from the exterior opening of the fistula tract 3. Whilst pulling on the spring 412 and removing it from the body through the anal canal 4. The ends 50 and 54 of the seton 442 are then brought together to form a loop, and ends 50 and 54 of the suture 442a tied together in a knot (not shown) to hold the hollow seton in the loop shape. Suitably, the knot may subsequently be manoeuvred to a location within the cavity 72 of the hollow seton 442, to improve patient comfort. Once formed into a loop, the seton 442 (and associated suture 442*a*) maintain the tract 3 open for drainage and other purposes, as described above.

In a variation on the probe 400 shown in FIG. 15, the sheath 416 on the leading end 426 may be dispensed with. Tests on probes manufactured according to the principles of the present invention have shown that the probes can work adequately without a sheath extending over an entire length of the spring, and indeed over a leading end of the probe (in particular the leading end of the spring). Factors impacting upon a decision as to whether to dispense with the sheath, in particular on a leading end of the probe, include: a diameter of the probe; a pitch of the spring (and so dimensions of any gaps between adjacent turns of the spring, which may only open up when the probe is deformed during passage along a fistula tract); and materials chosen to form the spring (and in particular their coefficient of friction).

The medical probe of the present invention has been described with particular reference to a fistula probe, intended for traversing a fistula tract. It will be appreciated however that the probe has other uses within the medical field, in particular for traversing other tracts in the body, including but not restricted to a tendon or ligament sheath, as well as tracts forming part of the vascular system such as arteries and veins. Any of the medical probes, assemblies comprising medical probes, treatment elements and methods described herein may have a use in further procedures, such as the traversal and/or treatment of such further tracts, and the performance of steps in methods which involve passing the probe into/along any such tracts.

Various modifications may be made to the foregoing without departing from the spirit or scope of the present invention.

For example, the sheath may be formed from an elongate element which is helically wound on to the elastically deformable member so as to cover the member, and which may be an elongate wrapping element. The elongate element may comprise a tape, strap or strip. Successive turns of the helically wound elongate element may overlap a preceding turn.

The invention claimed is:

1. A fistula probe assembly comprising a fistula probe for traversing a fistula tract in a body of a patient, and a flexible elongate tubular seton;
in which the fistula probe comprises:
an elongate elastically deformable member having a leading end, a trailing end, an outer surface and a longitudinal axis, the elastically deformable member comprising a helically wound element in the form of a spring having a plurality of coils, in which the spring is arranged so that coils which are adjacent, taken in a direction along the longitudinal axis, are in abutment in at least a rest configuration of the elastically deformable member;
a sheath having an inner surface which contacts the outer surface of the elastically deformable member, the sheath extending from the leading end of the elastically deformable member only part-way along a length of the elastically deformable member, so that the outer surface of the elastically deformable member is only covered by the sheath along a leading end portion of the elastically deformable member; and
a closed leading end adapted to be inserted into the fistula tract, the leading end being shaped to facilitate insertion of the probe into the tract;
and in which:
the flexible elongate tubular seton extends over the trailing end and a portion of the outer surface of the elastically deformable member; and
the flexible elongate tubular seton is releasably coupled to the elastically deformable member, so that the seton can be drawn into the tract by the elastically deformable member and then released from the elastically deformable member leaving the seton in place within the tract;
wherein the seton has an inner surface that contacts the outer surface of the elastically deformable member.

2. A fistula probe assembly as claimed in claim 1, in which the elastically deformable member has a first, rest configuration which the member adopts in the absence of an external load, the member being substantially straight when in the rest configuration.

3. A fistula probe assembly as claimed in claim 2, in which the elastically deformable member is movable to a second configuration on application of an external load, a restorative force of the elastically deformable member acting to urge the member to its rest configuration in the absence of the external load.

4. A fistula probe assembly as claimed in claim 1, in which the sheath is tubular, fitted over the elastically deformable member and deformed into contact with the outer surface of the elastically deformable member.

5. A fistula probe assembly as claimed in claim 1, in which the seton comprises first and second open ends and a passage extending along a length of the seton between the open ends.

6. A fistula probe assembly as claimed in claim 1, in which the elastically deformable member has a first portion of a first diameter, and a second portion of a second diameter, the second diameter being smaller than the first diameter.

7. A fistula probe assembly as claimed in claim 1, comprising a flexible elongate treatment element.

8. A fistula probe assembly as claimed in claim 7, in which the treatment element is coupled to the elastically deformable member via the seton.

9. A fistula probe assembly as claimed in claim 8, in which the treatment element is located within the seton.

10. A fistula probe assembly as claimed in claim 1, in which the leading end of the probe is tapered, and in which the probe tapers from a first outside diameter to a second smaller diameter at a lead-most part of the leading end.

11. A fistula probe as claimed in claim 10, in which the leading end is defined by an end component which is coupled to the elastically deformable member.

12. A fistula probe assembly as claimed in claim 1, comprising a coupling feature for coupling a further component to the probe.

13. A fistula probe assembly as claimed in claim 12, in which the further component is selected from the group comprising a cleaning tool and a suture.

14. A fistula probe assembly as claimed in claim 12, in which the coupling feature is provided on the elastically deformable member.

15. A fistula probe assembly as claimed in claim 1, comprising a connecting element for joining a first end of the seton to a second end of the seton.

16. A fistula probe assembly as claimed in claim 15, in which the seton comprises first and second tubular ends, and in which the connecting element is insertable into the first and second tubular ends to join the ends together.

17. A probe assembly as claimed in claim 1, in which the sheath extends over the leading end of the elastically deformable member to form the closed leading end of the probe.

18. A method of treating a fistula tract in a body of a patient using the fistula probe assembly of claim 1, the method comprising the steps of:
coupling a first end of the seton to the fistula probe;
inserting the leading end of the probe into a first opening of a fistula tract trailing the seton;
maneuvering the probe along the tract and out of a second opening of the tract;
removing the probe from the tract through the second opening;
releasing the seton from the probe;
removing the probe from the body of the patient leaving the seton in place within the tract, a first portion of the seton comprising the first end extending from the second opening of the tract, and a second portion of the seton comprising a second end extending from the first opening of the tract; and
coupling the first end of the seton to the second end to form a loop and thereby retain the seton within the tract.

19. A fistula probe assembly as claimed in claim 1, wherein the seton has a leading end that is positioned proximal to a trailing end of the sheath along the longitudinal axis.

20. A fistula probe assembly as claimed in claim 19, wherein the leading end of the seton is longitudinally spaced apart from the trailing end of the sheath along the longitudinal axis.

21. A fistula probe assembly as claimed in claim 1, wherein the seton is configured to be released from the elastically deformable member by pulling the sheath relative to the seton in a direction extending from the trailing end to the leading end of the elastically deformable member.

22. A fistula probe assembly as claimed in claim 1, wherein the sheath acts to partially restrict return movement of the covered portion of the elastically deformable member back to a rest configuration when an external load deforms the elastically deformable member.

23. A fistula probe assembly comprising a fistula probe for traversing a fistula tract in a body of a patient, and a flexible elongate tubular seton;
in which the fistula probe comprises:
an elongate elastically deformable member having a leading end, a trailing end, an outer surface and a longitudinal axis, the elastically deformable member comprising a helically wound element in the form of a spring having a plurality of coils, in which the spring is arranged so that coils which are adjacent, taken in a direction along the longitudinal axis, are in abutment in at least a rest configuration of the elastically deformable member;
a sheath having an inner surface which contacts the outer surface of the elastically deformable member, the sheath extending from the leading end of the elastically deformable member only part-way along a length of the elastically deformable member, so that the outer surface of the elastically deformable member is only covered by the sheath along a leading end portion of the elastically deformable member; and
a closed leading end adapted to be inserted into the fistula tract, the leading end being shaped to facilitate insertion of the probe into the tract;
and in which:
the flexible elongate tubular seton extends over the trailing end and a portion of the outer surface of the elastically deformable member;
the flexible elongate tubular seton is releasably coupled to the elastically deformable member, so that the seton can be drawn into the tract by the elastically deformable member and then released from the elastically deformable member leaving the seton in place within the tract; and
the seton is arranged to engage the elastically deformable member in an interference fit.

24. A fistula probe assembly comprising a fistula probe for traversing a fistula tract in a body of a patient, and a flexible elongate tubular seton;
in which the fistula probe comprises:
an elongate elastically deformable member having a leading end, a trailing end, an outer surface and a longitudinal axis, the elastically deformable member comprising a helically wound element in the form of a spring having a plurality of coils, in which the spring is arranged so that coils which are adjacent, taken in a direction along the longitudinal axis, are in abutment in at least a rest configuration of the elastically deformable member;
a sheath having an inner surface which contacts the outer surface of the elastically deformable member, the sheath extending from the leading end of the elastically deformable member only part-way along a length of the elastically deformable member, so that the outer surface of the elastically deformable member is only covered by the sheath along a leading end portion of the elastically deformable member; and
a closed leading end adapted to be inserted into the fistula tract, the leading end being shaped to facilitate insertion of the probe into the tract;
and in which:
the flexible elongate tubular seton extends over the trailing end and a portion of the outer surface of the elastically deformable member;
the flexible elongate tubular seton is releasably coupled to the elastically deformable member, so that the seton can be drawn into the tract by the elastically deformable member and then released from the elastically deformable member leaving the seton in place within the tract;
the elastically deformable member has a first portion of a first diameter, and a second portion of a second diameter, the second diameter being smaller than the first diameter; and
the seton is arranged to engage the second portion of the elastically deformable member, and does not extend on to the first portion.

25. A fistula probe assembly comprising a fistula probe for traversing a fistula tract in a body of a patient, and a flexible elongate tubular seton;
in which the fistula probe comprises:
an elongate elastically deformable member having a leading end, a trailing end, an outer surface and a longitudinal axis, the elastically deformable member comprising a helically wound element in the form of a spring having a plurality of coils, in which the spring is arranged so that coils which are adjacent, taken in a direction along the longitudinal axis, are in abutment in at least a rest configuration of the elastically deformable member;

a sheath having an inner surface which contacts the outer surface of the elastically deformable member, the sheath extending from the leading end of the elastically deformable member only part-way along a length of the elastically deformable member, so that the outer surface of the elastically deformable member is only covered by the sheath along a leading end portion of the elastically deformable member; and a closed leading end adapted to be inserted into the fistula tract, the leading end being shaped to facilitate insertion of the probe into the tract;

and in which:

the flexible elongate tubular seton extends over the trailing end and a portion of the outer surface of the elastically deformable member; and the flexible elongate tubular seton is releasably coupled to the elastically deformable member, so that the seton can be drawn into the tract by the elastically deformable member and then released from the elastically deformable member leaving the seton in place within the tract;

wherein the fistula probe assembly further comprises a flexible elongate treatment element; and wherein the treatment element extends within an internal cavity defined by the elastically deformable member.

26. A fistula probe assembly comprising a fistula probe for traversing a fistula tract in a body of a patient, and a flexible elongate tubular seton;

in which the fistula probe comprises:

an elongate elastically deformable member having a leading end, a trailing end, an outer surface and a longitudinal axis, the elastically deformable member comprising a helically wound element in the form of a spring having a plurality of coils, in which the spring is arranged so that coils which are adjacent, taken in a direction along the longitudinal axis, are in abutment in at least a rest configuration of the elastically deformable member;

a sheath having an inner surface which contacts the outer surface of the elastically deformable member, the sheath extending from the leading end of the elastically deformable member only part-way along a length of the elastically deformable member, so that the outer surface of the elastically deformable member is only covered by the sheath along a leading end portion of the elastically deformable member; and a closed leading end adapted to be inserted into the fistula tract, the leading end being shaped to facilitate insertion of the probe into the tract;

and in which:

the flexible elongate tubular seton extends over the trailing end and a portion of the outer surface of the elastically deformable member; and the flexible elongate tubular seton is releasably coupled to the elastically deformable member, so that the seton can be drawn into the tract by the elastically deformable member and then released from the elastically deformable member leaving the seton in place within the tract;

wherein the fistula probe assembly further comprises a flexible elongate treatment element; and wherein part of the treatment element is located between an inner surface of the seton and the outer surface of the elastically deformable member.

27. A fistula probe assembly comprising a fistula probe for traversing a fistula tract in a body of a patient, and a flexible elongate tubular seton;

in which the fistula probe comprises:

an elongate elastically deformable member having a leading end, a trailing end, an outer surface and a longitudinal axis, the elastically deformable member comprising a helically wound element in the form of a spring having a plurality of coils, in which the spring is arranged so that coils which are adjacent, taken in a direction along the longitudinal axis, are in abutment in at least a rest configuration of the elastically deformable member;

a sheath having an inner surface which contacts the outer surface of the elastically deformable member, the sheath extending from the leading end of the elastically deformable member only part-way along a length of the elastically deformable member, so that the outer surface of the elastically deformable member is only covered by the sheath along a leading end portion of the elastically deformable member; and a closed leading end adapted to be inserted into the fistula tract, the leading end being shaped to facilitate insertion of the probe into the tract;

and in which:

the flexible elongate tubular seton extends over the trailing end and a portion of the outer surface of the elastically deformable member;

the flexible elongate tubular seton is releasably coupled to the elastically deformable member, so that the seton can be drawn into the tract by the elastically deformable member and then released from the elastically deformable member leaving the seton in place within the tract; and wherein the seton is located around the outer surface of the elastically deformable member and extends over the trailing end, the seton having an inner surface which contacts the outer surface of the elastically deformable member; and in which a further treatment element is located within the seton and coupled to the elastically deformable member via the seton.

28. A fistula probe assembly as claimed in claim 27, in which the treatment element is a flexible elongate treatment element for performing a medical procedure in the body.

29. A fistula probe assembly comprising a fistula probe for traversing a fistula tract in a body of a patient, and a flexible elongate tubular seton;

in which the fistula probe comprises:

an elongate elastically deformable member having a leading end, a trailing end, an outer surface and a longitudinal axis, the elastically deformable member comprising a helically wound element in the form of a spring having a plurality of coils, in which the spring is arranged so that coils which are adjacent, taken in a direction along the longitudinal axis, are in abutment in at least a rest configuration of the elastically deformable member;

a sheath having an inner surface which contacts the outer surface of the elastically deformable member, the sheath extending from the leading end of the elastically deformable member only part-way along a length of the elastically deformable member, so that the outer surface of the elastically deformable member is only covered by the sheath along a leading end portion of the elastically deformable member; and a closed leading end adapted to be inserted into the fistula tract, the leading end being shaped to facilitate insertion of the probe into the tract;

and in which:

the flexible elongate tubular seton extends over the trailing end and a portion of the outer surface of the elastically deformable member; and the flexible elongate tubular seton is releasably coupled to the elastically deformable member, so that the seton can be drawn into the tract by the elastically deformable member and then released from the elastically deformable member leaving the seton in place within the tract;

wherein the fistula probe assembly further comprises a connecting element for joining a first end of the seton to a second end of the seton;

wherein the seton comprises first and second tubular ends, and wherein the connecting element is insertable into the first and second tubular ends to join the ends together;

wherein a portion of the seton at one of the first and second ends is adapted to be rolled back and the connecting element is insertable in said portion of the seton; and the portion of the seton that has been rolled back is adapted to then be rolled forward over a portion of the connecting element.

* * * * *